United States Patent
Arndt

(10) Patent No.: US 6,841,188 B1
(45) Date of Patent: Jan. 11, 2005

(54) METHOD OF DEVELOPING LATENT FINGERPRINTS

(75) Inventor: Douglas C. Arndt, Jacksonville, FL (US)

(73) Assignee: Armor Holdings Forensics, Inc., Jacksonville, FL (US)

( * ) Notice: Subject to any disclaimer, the term of this patent is extended or adjusted under 35 U.S.C. 154(b) by 0 days.

(21) Appl. No.: 10/776,120

(22) Filed: Feb. 11, 2004

(51) Int. Cl.$^7$ .............................................. A61B 5/117
(52) U.S. Cl. .............................. 427/1; 427/7; 427/157; 427/261; 427/265; 427/288; 427/353
(58) Field of Search ................................ 427/1, 7, 352, 427/353, 157, 261, 265, 288

(56) References Cited

U.S. PATENT DOCUMENTS 3,960,632 A * 6/1976 Gaines et al. ............... 156/245
4,029,012 A    6/1977 Smith, III et al.
4,182,261 A    1/1980 Smith, III et al.
4,262,623 A    4/1981 Smith, III et al.
4,983,415 A    1/1991 Arndt
6,488,750 B1  12/2002 Arndt

* cited by examiner

Primary Examiner—Kirsten C. Jolley
(74) Attorney, Agent, or Firm—Harold L. Jackson

(57) ABSTRACT

A method of developing latent fingerprints involves the preparation of an 8-quinolinol complex by mixing a solution of 8-hydroxyquinoline or a derivative with a complexing reagent such as a metal salt. The solution is then applied to a porous substrate, such as paper, containing the latent fingerprint where the soluble complex is adsorbed onto the surface of the latent print and precipitates thereon. The unadsorbed solution is then removed from the substrate allowing the precipitate to highlight the latent image. The choice of the complexing reagent will determine the color of the precipitate and whether or not it is flourescent.

13 Claims, No Drawings

METHOD OF DEVELOPING LATENT FINGERPRINTS

FIELD OF THE INVENTION

The present invention relates to the development of latent fingerprints and particularly to the development of such prints on a porous substrate.

DESCRIPTION OF THE PRIOR ART

The term "physical developer" as used in the forensic finger print art refers to the visualization of the oily components deposited by the ridge pattern of a person's fingertip i.e., fingerprint area, onto a porous substrate such as paper. It is to be noted that the term "fingerprint" or "fingerprint area" as used herein includes palm as well as foot prints. Typically the physical developer technique involves the reduction of a silver salt, in solution, to elemental silver which precipitates and adsorbs onto the surface of latent prints thus developing them physically so that they may be visualized as gray images. This method has several shortcomings. First, the silver salt (silver nitrate) is costly, toxic, readily reduced by organic contaminants, and is typically unstable when exposed to light. Second, the method also involves several steps and typically requires lengthy development time to visualize the latent prints. Third, the documents must generally be pretreated with an acid solution in order to reduce darkening of the paper background containing the latent prints. Fourth, the redox chemicals are hazardous. Fifth, the process typically requires the use of purified, distilled water. Sixth, the processing equipment must be kept scrupulously clean to prevent reduction of the silver salt. Seventh, the working solution is unstable and is generally usable only for several hours up to a few days if properly stored away from light. Eighth, the processed documents continue to darken over time when exposed to air and light which drowns out the visualized prints unless they are treated with bleach. Ninth, the visualized prints, because they are grey, cannot be readily seen on black, dark, or deeply colored papers. Tenth, the spent chemicals are considered hazardous waste.

I have discovered a method utilizing 8-quinolinolate complexes formed by many of the reagents utilized in inkless fingerprint systems, which overcomes the above problems. Inkless systems have been developed for enabling a user to take the fingerprints of an individual while present as contrasted with the development of a latent fingerprint. Such inkless systems rely on the reaction of two chemical reagents at the time of fingerprint development. Typically a nonstaining first reagent (color formers) such as a transition metal salt is applied to a person's fingertips and a second reagent (developer), such as 8-hydroxyquinoline or it's derivative, is pre-applied to or inherent in the recording medium such as paper. The reagents remain isolated until the fingerprint is taken. See, for example, U.S. Pat. Nos. 4,029,012 ("'012 patent"); 4,182,261 and 4,262,623. More recently the use of a chealting agent has allowed the two reagents in solution to be located in the same container by preventing the reagents from chemically reacting until exposed to the moisture from the skin and/or the recording medium. See U.S. Pat. No. 6,488,750.

SUMMARY OF THE INVENTION

The present invention relies on a solution of an 8-quinolinolate complex formed by the reaction of such reagents to provide a colorant product, e.g., white, yellow, brown, green, grey, black, etc., or a colorless, but flourescent, product which is adsorbed onto the oily surface formed by the ridge pattern of a latent fingerprint deposited on a porous substrate such as paper to develop the print. In accordance with the present invention, an 8-quinolinate complex formed, for example, by a solution of 8-quinolinol or 8-hydroxyquinoline, or it's derivatives (hereinafter collectively referred to as "8-quinolinol"), and a sufficient amount of transition metal salt to form a complexed reaction product. A description of 8-hydroxyquinoline derivatives is set forth in the '012 patent and the contents of that patent are incorporated herein by reference. The solution is then applied to a porous substrate, such as paper, containing the latent fingerprint. The soluble complex from the solution is adsorbed onto the oily surface left by the latent print and subsequently precipitates. The solution absent the precipitate is then removed from the substrate, for example, by a water rinse, leaving a two dimensional image (color or colorless, but flourescent) of the ridge pattern of the person's finger.

The features and steps of the present invention, which are believed to be novel, are set forth in the appended claims. The invention, as to its organization and advantages, may best be understood by reference to the following description.

DESCRIPTION OF THE PREFERRED EMBODIMENT

In accordance with the present invention, as a first step, a solution of an 8-quinolinolate complex is prepared for subsequent application to a porous substrate, e.g., paper, containing the latent fingerprint to be developed.

Generically an 8-quinolinolate complex may be illustrated as follows:

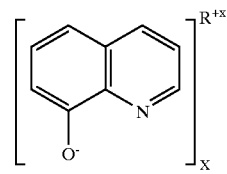

Where X=valence of complexed ion and

Where R=positively charged complexing ion (radical), e.g., metal ammonium or amino (—NH$_2$) group ion.

Examples of 8-quinolinate derivative complexes are illustrated below:

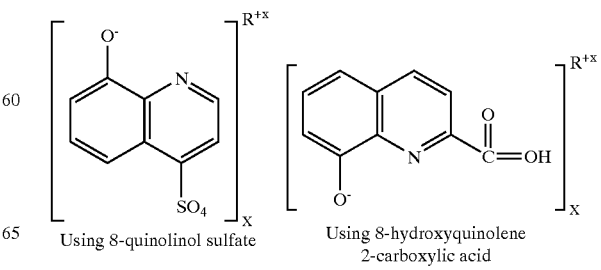

Using 8-quinolinol sulfate  Using 8-hydroxyquinolene 2-carboxylic acid

-continued

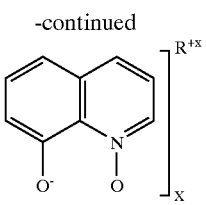

Using 8-hydroxyquinoline N-oxide

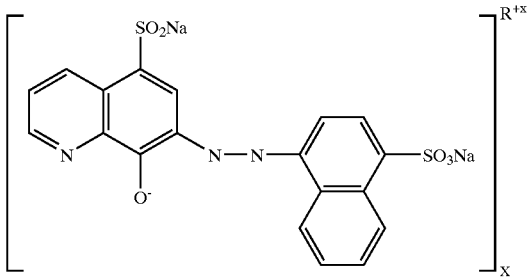

Using 8-hydroxy-7-(2-sulfo-1-naphthylazo)-
5-quinoline-sulfonic acid, disodium salt

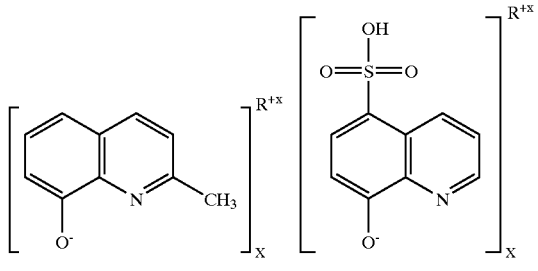

Using 2-methyl 8-quinolinol    Using 8-hydroxyquinoline
5-sulfonic acid

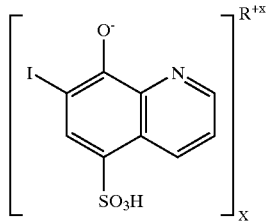

Using 8-hydroxyquinoline 7-iodo
5-sulfonic acid

Examples of 8-quinoline complexed with a metal salt are illustrated below:

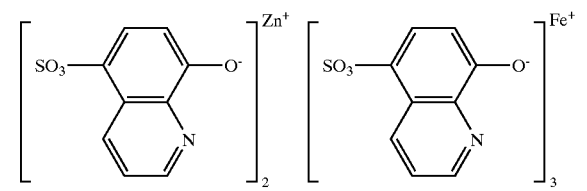

An aqueous solution of one or more metal salts and 8-hydroxyquinoline sulfate, preferably in stoichiometric amounts, produce stable complexes that may be colored, e.g., white, yellow, brown, green, grey, black, or essentially colorless, but flourescent, or a combination thereof. The method employs the phenomenon of phase transition whereby the soluble complex is adsorbed onto the oily surface of the latent print where it is insoluble and subsequently precipitates. A phase transition catalyst may be employed to expedite the process, but this is typically not necessary. Optimal results are obtained from very dilute solutions of the metal salt, usually in the range of about 0.005% to 0.1% molar concentrations. The 8-hydroxyquinoline compound is preferably stoichiometrically concentrated according to the valence of the metal ion(s).

It should be noted that metals, such as copper and silver, are not easy to work with because of the insoluble precipitates that are formed. Other metals, such as barium and arsenic, are toxic and thus generally undesirable. Excellent results have been obtained using the chloride salts of the following metals: Li, Ca, Sr, Cr, Ni, Co, Fe, Al, Zr, Mn, and Zn. Mg, Mo, Ti, V and Ga are also candidates. Any water soluble salt of the metals may be used, but pH can have a impact on fluorescence and on the solubility of reaction product. The sulfate of 8-quinolinol is preferred as the complexing agent because of cost, availability, and high water solubility.

To visualize latent prints using this method on white or pale paper, it is preferably to use a metal that produces a colored complexes such as iron. On dark papers a metal producing a flourescent complex using aluminum, calcium, or zinc is preferred or a nonmetal ionic molecule such as ammonium. A mixture of complexed metals may be used to produce latent prints that are both colored and flourescent so as to make the working solution universal with respect to all hues of paper.

Examples of specific formulations and the results:

Colored Fingerprints: A 0.18750 molar solution of 8-hydroxyquinoline sulfate with a 0.00625 molar concentration of ferric chloride is prepared in water. A piece of white bond paper having substantially oily, latent print residues was immersed into the solution for about three seconds, then immediately rinsed in running tap water. The result was dark grey fingerprints visible against lighter grey background.

Flourescent Fingerprints: 0.00625 M aqueous solutions of the chlorides of lithium, calcium, strontium, manganese, aluminum, chromium, and zinc were prepared. To each solution, a stoichiometric amount of 8-hydroxyquinoline sulfate was admixed. Strips of black, gel-pen paper having oily fingerprints thereon was immersed for about three seconds into each of the solutions, then immediately rinsed in running tap water. The result from every solution was highly fluorescent, green fingerprints visible in long-wave ultra-violet light. The shelf life of these solutions seems to be indefinite.

Mixing the solutions of ferric chloride with zinc chloride and 8-quinolinol sulfate produced fingerprints on a variety of papers visible as either grey in ordinary light or as fluorescent green in ultra-violet light.

The colored method is premixed as "A" (8-hydroxyquinoline sulfate) and "B" (metal salt) solutions which have indefinite shelf lives. They are mixed in equal volumes to prepare a working solution that is usable for 2–3 weeks. The fluorescent method is premixed as a single working solution having an indefinite shelf life.

The present invention provides a simple and effective method of developing latent prints on a variety of porous substrates. Various modifications of the preferred embodiment may occur to those skilled in the art without involving a departure from the spirit and scope of the invetnion as defined by the appended claims.

What is claimed is:
1. A method of developing latent fingerprints deposited on a porous substrate comprising:

a) providing an 8-quinolinol complex solution;

b) applying the solution to the porous substrate containing the latent fingerprint whereby the soluble complex is adsorbed onto the oily surface of the latent print and precipitates thereon; and c) removing the unadsorbed solution from the substrate to allow the precipitate to highlight the latent image.

2. The method of claim 1 wherein step (c) comprises rinsing the substrate with water.

3. The method of claim 1 wherein the 8-quinolinol is complexed with a metal salt.

4. The method of claim 3 wherein the transition metal is one or more metals selected from the group consisting of Fe, Li, Ca, Sr, Cr, Ni, Co, Al, Zr, Zn, Mg, Mo, Ti, V, Mn and Ga.

5. The method of claim 1 wherein the 8-quinoline is complexed with ammonium or an amino acid reagent.

6. The method of claim 2 wherein the substrate is paper.

7. A method of developing latent fingerprints deposited on a porous substrate comprising:

a) providing a solution of 8-hydroxyquinoline or a derivative thereof and a sufficient amount of a metal salt to form a complexed product;

b) applying the solution to the porous substrate containing the latent image whereby the soluble complex is adsorbed onto the oily surface of the latent print and precipitates thereon; and c) removing the unadsorbed solution from the substrate to allow the precipitates to highlight the latent image.

8. The method of claim 7 wherein step (c) comprises rinsing the substrate with water.

9. The method of claim 8 wherein the metal is one or more metals selected from the group consisting of Fe, Li, Ca, Sr, Cr, Ni, Co, Al, Zr, Zn, Mg, Mo, Ti, V, Mn and Ga.

10. A method of developing latent fingerprints deposited on a porous substrate comprising:

a) providing a solution of a 8-hydroxyquinoline or derivative and a complexing reagent characterized by the following structure:

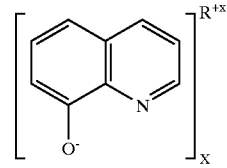

where X valence of the complexed ion where R=positively charged complexed ion which forms a colorant or flourescent compound with 8-hydroxyquinoline and its derivatives, b) applying the solution to the porous substrate containing the latent fingerprint whereby the soluble complex is adsorbed onto the oily surface of the latent print and precipitates thereon; and c) removing the unadsorbed solution from the substrate to allow the precipitate to highlight the latent image.

11. The method of claim 10 wherein the 8-hydroxyquinoline or derivative is complexed with a metal salt.

12. The method of claim 11 wherein the metal is one or more metals selected from the group consisting of Fe, Li, Ca, Sr, Cr, Ni, Co, Al, Zr, Zn, Mg, Mo, Ti, V, Mn and Ga.

13. The method of claim 10 wherein the 8-quinoline is complexed with ammonium or an amino acid reagent.

* * * * *

UNITED STATES PATENT AND TRADEMARK OFFICE
CERTIFICATE OF CORRECTION

PATENT NO. : 6,841,188 B1
DATED : January 11, 2005
INVENTOR(S) : Douglas C. Arndt It is certified that error appears in the above-identified patent and that said Letters Patent is hereby corrected as shown below:

Column 3,
Lines 5-7, 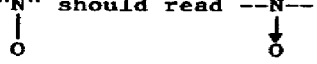

Line 10, "SO$_2$Na" should read -- SO$_3$Na --
Line 15, "N-N" should read -- N=N --.
Line 50, "Zn$^+$" should read -- Zn$^{+2}$ --.
Line 50, "Fe$^+$" should read -- Fe$^{+3}$ --.

Column 6,
Line 15, "X valance" should read -- X=valence --.

Signed and Sealed this

Twelfth Day of April, 2005

JON W. DUDAS
*Director of the United States Patent and Trademark Office*